(12) United States Patent
Lee

(10) Patent No.: US 6,955,663 B2
(45) Date of Patent: Oct. 18, 2005

(54) CATHETER FOR EXTRACTING AND INSERTING HUMORS

(76) Inventor: Keun-Ho Lee, #1333-1902 Greentown, 1185-2 Joong-dong, Wonmi-gu, Seoul (KR)

( * ) Notice: Subject to any disclaimer, the term of this patent is extended or adjusted under 35 U.S.C. 154(b) by 23 days.

(21) Appl. No.: 10/126,242

(22) Filed: Apr. 19, 2002

(65) Prior Publication Data

US 2003/0199829 A1 Oct. 23, 2003

(51) Int. Cl.7 .............................................. A61M 25/00
(52) U.S. Cl. ........................................................ 604/284
(58) Field of Search .............................. 604/540, 541, 604/523, 533–535, 537–539, 284, 285, 166.01

(56) References Cited

U.S. PATENT DOCUMENTS

| | | | | |
|---|---|---|---|---|
| 4,796,615 A | * | 1/1989 | Bullock et al. | 128/202.27 |
| 5,088,984 A | * | 2/1992 | Fields | 604/167.02 |
| 5,234,417 A | * | 8/1993 | Parks et al. | 604/533 |
| 5,951,508 A | * | 9/1999 | Van Driel | 604/6.15 |
| 5,989,240 A | * | 11/1999 | Strowe | 604/533 |
| 6,511,472 B1 | * | 1/2003 | Hayman et al. | 604/533 |
| 6,575,960 B2 | * | 6/2003 | Becker et al. | 604/533 |
| 6,582,395 B1 | * | 6/2003 | Burkett et al. | 604/96.01 |
| 2002/0038114 A1 | * | 3/2002 | Segura | 604/533 |
| 2002/0084551 A1 | * | 7/2002 | Lee | 264/209.6 |
| 2003/0195478 A1 | * | 10/2003 | Russo | 604/247 |

FOREIGN PATENT DOCUMENTS

WO   WO 94/23775   * 10/1994 ............ A61M/5/32

* cited by examiner

Primary Examiner—Larry I. Schwartz
Assistant Examiner—Michael G. Bogart
(74) Attorney, Agent, or Firm—Hong, Degerman, Kang & Schmadeka

(57) ABSTRACT

The present invention provide a catheter which exhausts a humor such as a hematoma, a brain fluid, and an encephalophyma smoothly without any infection, and be able to inject a hematoma resolvent while maintaining a constant brain pressure, and is inserted into an accurate operative portion in the cranial cavity using a brain stereotactic frame conveniently and easily. The catheter 100 includes a long tube 110 made of an atoxic, transparent and flexible material; a two-way fitting 160 having two channels and inserted into a rear portion of the tube through a fitting 120; second and third coupling members 140 and 150 selectively coupled to a branched channel of the two-way fitting 160; an injection member 170 including a needle portion 174 inserted into a rear portion of the third coupling member 150 through an inserting hole 153; and a fourth coupling member 180 including a seal member 181 and being inserted into a reception groove 171 formed in a rear portion of the injection member 170.

4 Claims, 4 Drawing Sheets

CATHETER FOR EXTRACTING AND INSERTING HUMORS

BACKGROUND OF THE INVENTION

1. Field of the Invention

The present invention relates to a catheter, and more specifically to a catheter which exhausts a humor such as a hematoma, a brain fluid, and an encephalophyma smoothly without any infection, and be able to inject a hematoma resolvent while maintaining a constant brain pressure, and is inserted into an accurate operative portion in the cranial cavity using a brain stereotactic frame conveniently and easily.

2. Description of the Prior Art

An intracranial hematoma has been treated by a therapy that directly removes it through a craniotomy which is a kind of a neurosurgical operation. Recently, a therapy has been widely used that removes the intracranial hematoma directly or by a brain stereotactic frame by using a brain cross section radiography or a magnetic resonance (MR) radiography using a computer. Since the operation can be performed under a local anesthesia in a short time, this therapy is applied to patients who cannot be under a general anesthesia.

For example, in the case that a brain parenchyme has a hemorrhage therein, a location of a hematoma in a cranial cavity is exactly measured by a brain cross section radiography. A skull is perforated, and a catheter is inserted into the hematoma directly or by using the brain stereotactic instrument in order to exhaust the hematoma out of the cranial cavity therethrough.

An exhaust aspect of the hematoma depends on a condition of the hematoma (i.e., solidity or liquidity). The hematoma should be exhausted steadily rather than momentarily, and the catheter may remain in the cranial cavity for a period of days in order to steadily exhaust the remaining hematoma out of the cranial cavity therethrough. In particular, In case of a solid hematoma, a hematoma resolvent is injected into the hematoma through the catheter so that the hematoma may be easily exhausted.

FIG. 1 is a cross-sectional view illustrating a conventional catheter. The catheter 1 includes a long tube 2 in which an exhausting passage 2a is formed, a head portion 3 attached to one end of the tube 2, and a plurality of holes 4 formed in a portion of the tube 2 near to the head portion 3. The catheter 1 further includes a location indication scale (not shown) arranged in a longitudinal direction thereof.

The catheter 1 is made of a transparent, atoxic, and flexible material, and preferably made of a pure silicone rubber.

The tube 2 is inserted into the cranial cavity through a perforated portion of the skull (not shown) by a depth to place the head portion 3 in a central portion of a humor such as a hematoma and a tumor. The rest portion of the tube 2 passes through the perforated portion of the skull and is put at a distance of 3 cm to 4 cm under the scalp by use of a trocar.

The outer end of the cranial cavity of the tube 2 is coupled to a brain pressure controller (not shown) and to a humor collecting bursa (not shown), so that the humor in the cranial cavity flows out and is collected in the humor collecting bursa in state of being excluded from outside.

The head portion 3 and a radiation construction line 5 of a radiation construction material are to grasp a location of the catheter 1 inserted into the cranial cavity during a plain roentgenography for the skull.

However, the catheter 1 of FIG. 1 has the following disadvantages in that the catheter 1 has one exhausting passage 2a. In the case that there is a need for injecting a hematoma resolvent or a physiological salt solution, a humor such as a hematoma filled in the catheter has to be inserted into the cranial cavity again. Further, since the physiological salt solution has to be injected additionally by an inside volume of the catheter 1, a brain pressure is increased. Furthermore, there is a risk of an infection due to a repeated injection of the physiological salt solution, and the catheter 1 is inconvenient to manipulate.

In efforts to overcome the problems descibed above, Korean Patent No. 178113 discloses a catheter that the hematoma resolvent is easily injected without increasing the brain pressure, and the humor such as the hematoma filled in the catheter is not outflowed into the cranial cavity again, and thus there is no risk of an infection.

FIG. 2 is a cross-sectional view illustrating a catheter of Koean Patent No. 178113.

The catheter 10 includes a long tube 12, a head portion 13 attached to one end of the tube 12, a plurality of holes 14 formed in a portion of the tube 12 near to the head portion 13, and a location indication scale 15.

The tube 12 includes an exhausting tube 12a and an injection tube 12b. The exhausting tube 12a has a relatively large cross-section area. A humor in the cranial cavity is exhausted through the exhausting tube 12a. The injection tube 12b has a relatively small cross-section area. A hematoma resolvent is injected into the cranial cavity through the injection tube 12b. A through hole 13a is formed in the head 13 to communicate with the injection tube 12b.

An injection tube 16 is removably coupled to one end portion of the injectin tube 12b opposite to the head portion 13. The injection tube 16 has the same diameter as the injection tube 12b and thus communicates with the injection tube 12b.

A coupling member 17 is arranged to seal and secure a coupling portion between the injection tubes 12b and 16. The coupling portion between the injection tubes 12b and 16 is at a distance from the head portion 13 to be located outside the cranial cavity when the head portion 13 is located in the cranial cavity and the tube 12 is extended externally during a use of the catheter 10.

The injection tube 16 is separateed from the tube 12 and is cut to have a free end (not shown) when used. However, the injection tube 16 is manufactured to be coupled to the tube 12 by the coupling member 17 for the sake of custody and a surgerical convenience.

Another coupling member 18 couples the tube 12 to a tube 19 attached to a rear portion of the tube 12. One end of the injection tube 16 is inserted into an inner surface of the coupling member 18.

However, in the conventional catheter 10, the tube 12, the injection tube 16 and the coupling members 17 and 18 are configured to surround an outer circumference surface of the tubes 12 and 19. As a result, at least the coupling portion of the catheter 10 has an external diameter larger than those of the tubes 12 and 19.

Therefore, in case that a brain parenchyme has a hemorrhage therein, after measuring a location of the hematoma in the cranial cavity using the cross section radiography for a brain to perforate the skull, it is very difficult to insert the catheter 10 into the hematoma using a brain stereotactic frame (not shown).

In more detail, the brain stereotactic frame helps to determine an accurate location of the hematoma in the cranial cavity. But, a coupling portion of the catheter 10 corresponding to the injection tube 16 and the coupling members 17 and 18 has an external diameter larger than the tube 12. As a result, a through hole, which is formed by the brain stereotactic frame in order to prevent the catheter from being separated and has the almost same diameter as the tube 12, becomes narrow relatively due to the injection tube 16 and the coupling members 17 and 18. Consequently, the brain stereotactic frame becomes difficult to use, and a high skill is required to place the catheter in an accurate location.

In addition, it becomes very difficult to perforate the skull hypodermis layer using a trocar due to the injection 16 and the coupling members 17 and 18. Furthermore, since the conventional catheter has a complicated dual-tube structure, an inferiority rate is high, a cleaning and a sterilization are not easy, and a manufacturing cost is high.

SUMMARY OF THE INVENTION

To overcome the problems described above, preferred embodiments of the present invention provide a catheter which exhausts a humor such as a hematoma, a brain fluid, and an encephalophyma smoothly without any infection, and be able to inject a hematoma resolvent while maintaining a constant brain pressure, and is inserted into an accurate operative portion in the cranial cavity using a brain stereotactic frame conveniently and easily.

In order to achieve the above object, the preferred embodiments of the present invention provide a catheter comprising: a long tube made of an atoxic, transparent and flexible material; a two-way fitting having two channels and inserted into a rear portion of the tube through a fitting; second and third coupling members selectively coupled to a branched channel of the two-way fitting; an injection member including a needle portion inserted into a rear portion of the third coupling member through an inserting hole; and a fourth coupling member including a seal member and being inserted into a reception groove formed in a rear portion of the injection member.

BRIEF DESCRIPTION OF DRAWINGS

For a more complete understanding of the present invention and the advantages thereof, reference is now made to the following descriptions taken in conjunction with the accompanying drawings, in which like reference numerals denote like parts, and in which.

DESCRIPTION OF THE PREFERRED EMBODIMENTS

Reference will now be made in detail to preferred embodiments of the present invention, example of which is illustrated in the accompanying drawings.

Figure 3:
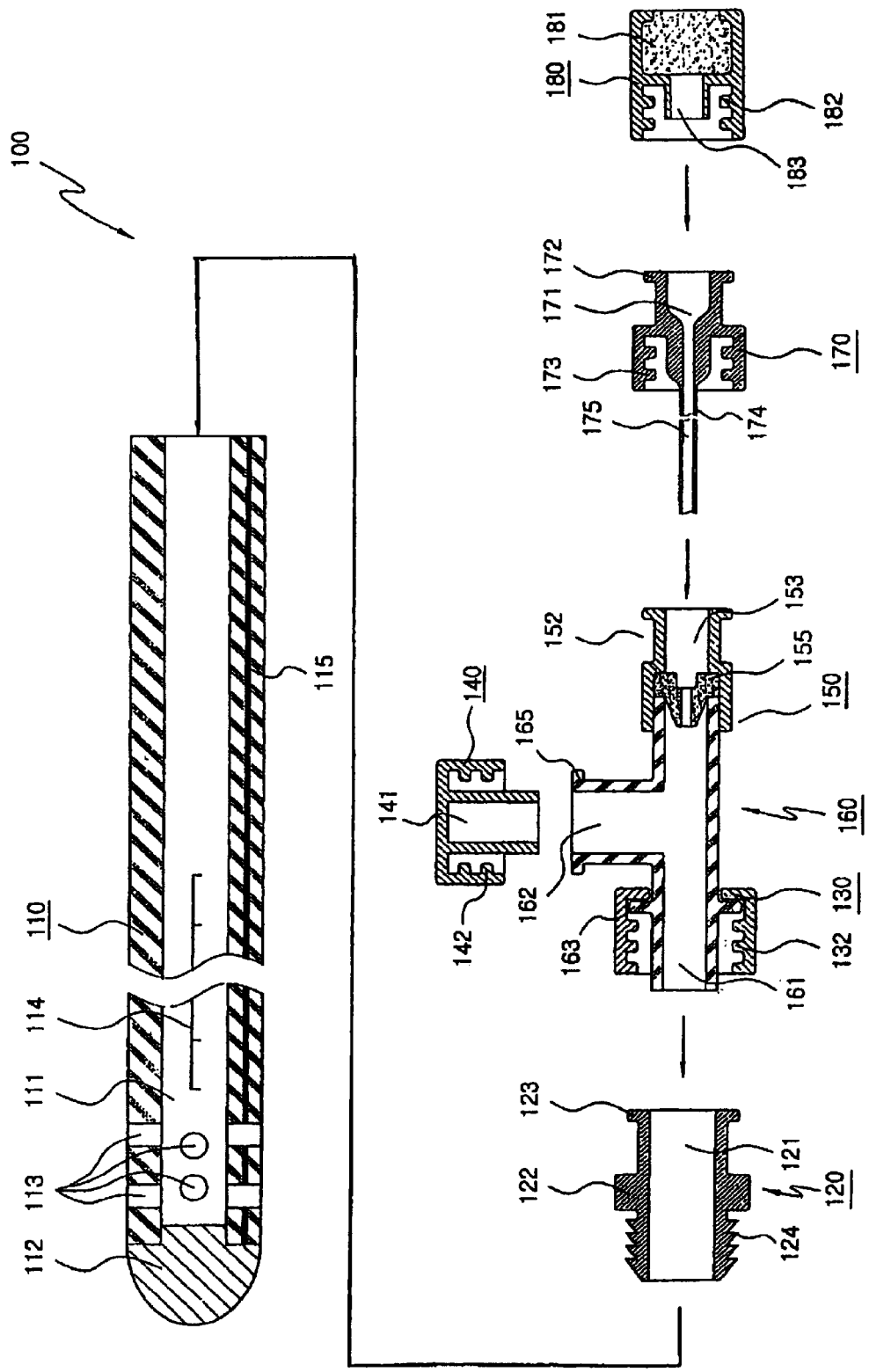
FIG. 3 is an exploded cross-sectional view illustrating a catheter according to the present invention.
Figure 4:
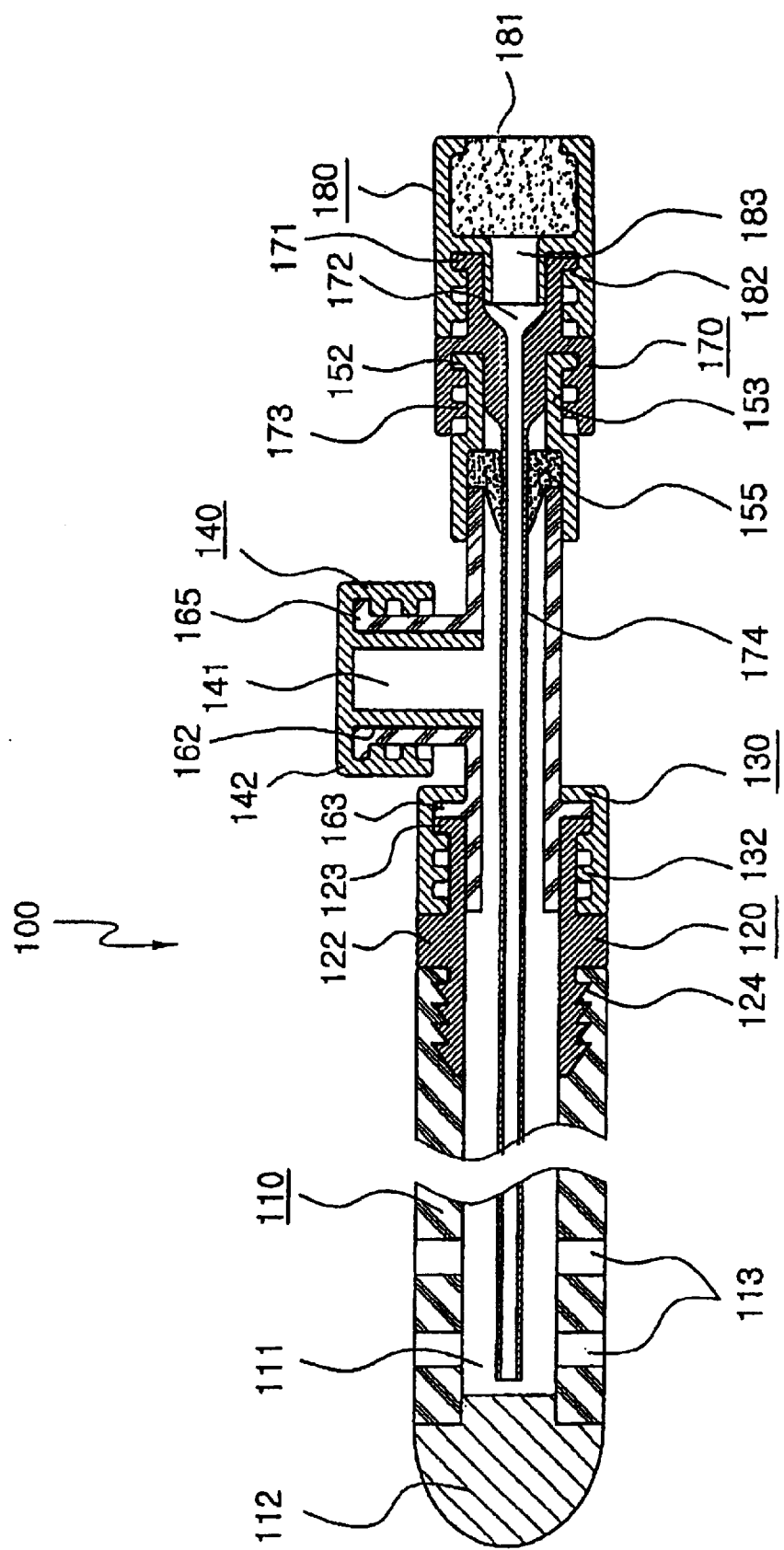
FIG. 4 is a cross-sectional view illustrating the catheter according to the present invention.

FIG. 3 is an exploded cross-sectional view illustrating a catheter according to the present invention. FIG. 4 is a cross-sectional view illustrating the catheter according to the present invention.

The catheter 100 includes a long tube 110, a fitting 120, first to fourth coupling members 130, 140, 150, and 180, a two-way fitting 160, and an injection member 170.

The tube 110 is made of an atoxic, transparent, and flexible material. The two-way fitting 160 has two channels and is inserted into a rear portion of the tube 110 through the fitting 120. The second and third members 140 and 150 are selectively coupled to the branched channels of the two-way fitting 160, respectively. A needle portion 174 of the injection member 170 is inserted into a rear portion of the third coupling member 150 through an inserting hole 153. The fourth coupling member 180 includes a sealing member 181 and is inserted into and coupled to a reception hole 171 of the injection 170.

The fitting 120 includes a saw-toothed portion 124 formed along a circumference of one end thereof and is tightly coupled to a rear portion of the tube 110. The fitting 120 further includes an edge protrusion 123 formed along an edge thereof. The edge protruding 123 is removably screw-coupled to the first coupling member 130 which is rotatably coupled to one side of the two-way fitting 160.

The two-way fitting 160 has a letter "T" shape and includes first and second channels 161 and 162 selectively formed therein. The first and second coupling members 130 and 140 are selectively coupled to an external circumference of the channels 161 and 162. A rear portion of the first channel 161 is coupled to the third coupling member 150 having a check valve 155 arranged therein.

The check valve 155 which is used as a backward flow prevention means prevents a humor a medicinal fluid from flowing out while inserting the injection member 170 through an incision groove (not shown) formed at a central portion thereof or after removing the injection member 170.

The third coupling member 150 includes an edge protrusion 152 formed in a rear portion thereof and is coupled to the injection member 170 through the edge protrusion 152.

The injection member 170 includes a needle portion 174 formed in a front portion thereof. The needle portion 174 has an injection passage 175 formed therein. The injection member 170 further includes an edge protrusion 172 formed in a rear portion along an external circumference thereof. The injection member 170 is coupled to the fourth coupling member 180 through the edge protrusion 172.

The catheter 100 includes the two-way fitting 160 that an injection and an exhaustion are selectively performed through the respective channels. Thus, the humor such as the hematoma, the brain fluid, and an encephalophyma can be exhausted smoothly through the two-way fitting 160 without causing any harmful side effect, and the hematoma resolvent can be injected easily while maintaining a constant brain pressure.

A method of using the catheter according to the present invention is described below.

The tube 110 includes an exhausting passage 111 which a single fluid channel is formed therein and has a constant external diameter. Such a tube 110 can be accurately inserted into the cranial cavity using the brain stereotactic frame.

When the tube 110 is inserted into the cranial cavity, the trocar is coupled to the rear portion of the tube 110. The trocar passes through the skull hypodermis layer and is taken out at a distance of about 30 mm from a first perforated portion of the skull. At this time, the first perforated portion of the skull is covered with a sterilization gauze in order to prevent an infection.

When a suture for the first perforated portion of the skull is completed, an exposed portion of the trocar around the first perforated portion of the skull is removed from the tube 110. At the same time, the fitting 120 is coupled to a rear portion of the tube 110, and then two-way fitting 160 having the second coupling member 140 coupled to the second channel 162 thereof is coupled to the fitting 120 inserted into the tube 110. Thereafter, the catheter 100 is stably secured to a head of a patient.

The injection member 170 coupled to the fourth coupling member 180 is coupled to the rear portion of the second coupling member 160 in such a manner that the needle portion 174 of the injection member 170 is inserted and passed through the incision groove (not shown) of the check valve 155 accommodated in the rear portion of the two-way fitting 160 by the third coupling member 150. The front portion of the needle portion 174 is inserted to a location adjacent to the head portion 112 of the tube 110 as shown in FIG. 4.

In order to prevent a brain pressure from being increased during a process of coupling the injection member 170, the second coupling member 140 is removed. Instead, the brain pressure controller (not shown) and the humor collecting bursa is coupled to the second channel 162, so that an overflowing of the humor occurred due to an insertion of the needle portion 174 is prevented, and the humor flows to the humor collecting bursa.

The medicinal substance or fluid is injected such that an injection needle is stuck into a seal member 181 of the fourth coupling member 180 without removing the fourth coupling member 180 from the injection member 170 or such that the fourth coupling member 180 removably coupled to the rear portion of the injection member 170 is removed and thereafter the medicinal substance or fluid is injected through the exposed reception groove 171 of the injection member 170.

Since the medicinal fluid is injected in the state that all fluid channels are shut tightly, it is possible to prevent the humor from being exhausted out during an injection.

The passage communicating with the brain pressure controller which is coupled to the second coupling member 140 is temporarily closed during an injection of the medicinal fluid.

Meanwhile, due to the check valve 155 arranged in the rear portion of the second coupling member 160, the humor or the medicinal fluid is not leaked out while the medicinal fluid is injected through the injection member 170 or even though the injection member 170 is removed after using it.

In the two-way fitting 160, the second channel 162 branched from the first channel is coupled to the brain pressure controller (not shown) after removing the second coupling member 140, so that the humor in the cranial cavity is rapidly exhausted through the path different from the third coupling member 150 coupled to the rear portion of the first channel 161.

Figure 1:
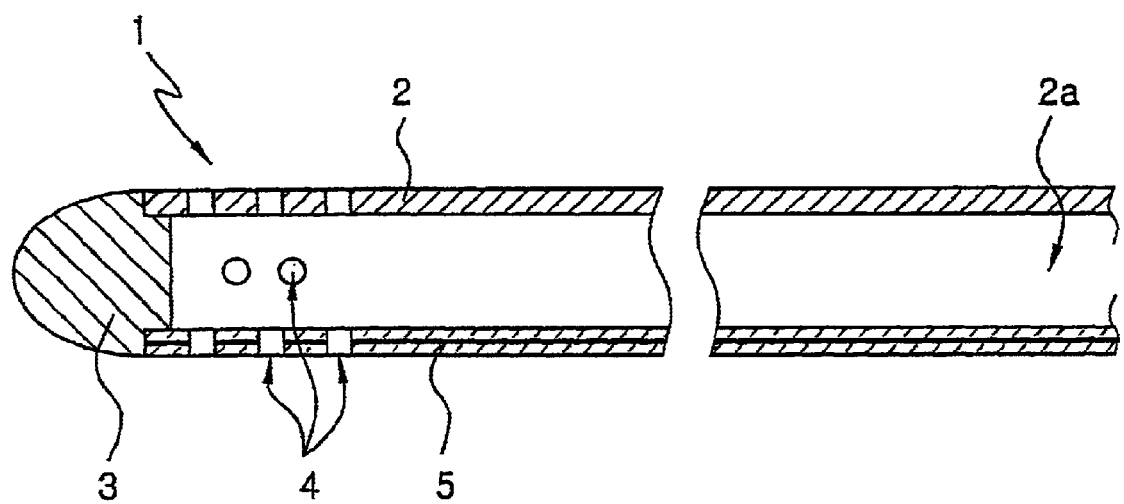
FIG. 1 is a cross-sectional view illustrating a conventional catheter.
Figure 2:
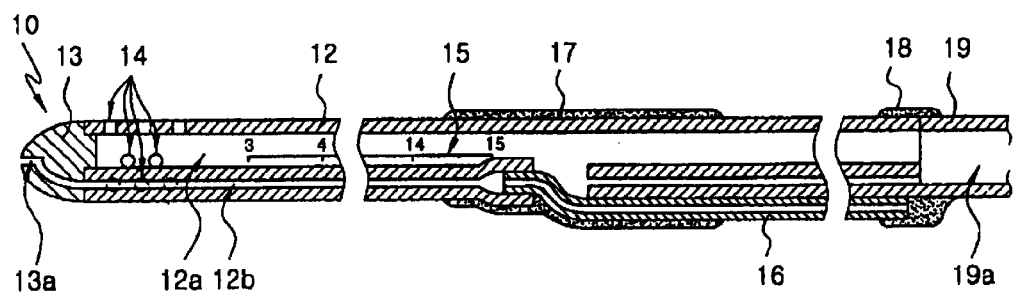
FIG. 2 is a cross-sectional view illustrating another conventional catheter.

The tube 110 has a large diameter than that of the dual-tube of FIG. 1 and thus has a high humor exhausting efficiency. Further, an external diameter of the tube 110 is uniform. Since the brain stereotactic frame can be used, an operation can be performed accurately and conveniently.

In addition, since the medicinal fluid is injected through the needle portion 174 of the injection member 170 which is made of a durable material more than the tube 110, the medicinal fluid is rapidly injected into the cranial cavity, and it is possible to prevent the tube 110 form being distorted. Further, the tube 110 is easy to manufacture, to clean and to sterilize.

As described herein before, the catheter according to the present invention includes the two-way fitting which selectively forms an injection passage and an exhausting passage. Therefore, it is possible to exhaust the humor such as the hematoma, a brain fluid, and an encephalophyma smoothly out of the cranial cavity without any harmful effect. Further, the hematoma resolvent can be injected easily while maintaining a constant brain pressure.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A catheter comprising:
    a long tube made of an atoxic, transparent and flexible material;
    a two-way fitting having two channels and inserted into a rear portion of the tube through a fitting;
    second and third coupling members selectively coupled to a branched channel of the two-way fitting;
    an injection member including a needle portion inserted in a rear portion of the third coupling member through an inserting hole; and
    a fourth coupling member including a seal member and being inserted into a reception groove formed in a rear portion of the injection member.

2. The catheter of claim 1, wherein the fitting includes a saw-toothed portion formed along a circumference of one end thereof, and an edge protrusion formed along an edge thereof, wherein the fitting is tightly coupled to a rear portion of the tube through the saw-toothed portion, and the edge protrusion is removably screw-coupled to a first coupling member which is rotatably coupled to one side of the two-way fitting.

3. The catheter of claim 1, wherein the two-way fitting has a letter "T" shape and includes first and second channels selectively formed therein, wherein the first and second coupling members are selectively coupled to an external circumference of the first and second channels, and a rear portion of the first channel is coupled to the third coupling member having a check valve arranged therein.

4. The catheter of claim 1, wherein the third coupling member includes an edge protrusion formed in a rear portion thereof and is coupled to the injection member through the edge protrusion, and the injection member includes a needle portion formed in a front portion thereof and an edge protrusion formed in a rear portion along an external circumference thereof, the needle portion having an injection passage formed therein, the injection member being coupled to the fourth coupling member through the edge protrusion.

* * * * *